United States Patent [19]

Crainich

[11] Patent Number: 5,275,583
[45] Date of Patent: Jan. 4, 1994

[54] TROCAR ASSEMBLY WITH INDEPENDENTLY ACTING SHIELD MEANS

[76] Inventor: Lawrence Crainich, P.O. Box 996, Charlestown, N.H. 03603

[21] Appl. No.: 956,155

[22] Filed: Oct. 5, 1992

[51] Int. Cl.⁵ .............................................. A61M 5/00
[52] U.S. Cl. ................................... 604/264; 604/164; 604/165; 604/167; 606/167; 606/184
[58] Field of Search ............... 604/158, 162, 164, 165, 604/169, 171, 264, 272, 274, 33, 166, 167, 249; 606/184

[56] References Cited

U.S. PATENT DOCUMENTS 4,601,710 7/1986 Moll .................................... 604/165

Primary Examiner—C. Fred Rosenbaum
Assistant Examiner—Noelle Kent Gring
Attorney, Agent, or Firm—Bachman & LaPointe

[57] ABSTRACT

A trocar assembly includes a trocar obturator having an outer diameter, a piercing tip and at least one, preferably a plurality of longitudinal cutouts; and a shield for the piercing tip, mounted in the longitudinal cutouts so as to be movable between an extended position and a retracted position, the shield being adapted to fit inside the longitudinal cutouts so as to shield the piercing tip when the shield is in the extended position, without exceeding the outer diameter of the trocar obturator. The trocar obturator may have a plurality of blades joined together to form the piercing tip, and the longitudinal cutouts may be formed between the blades. The shield preferably includes a plurality of independently acting shields mounted in the plurality of longitudinal cutouts, and further includes independent springs for independently biasing each shield of the plurality of shields toward the extended position wherein the piercing tip of the trocar obturator is shielded, and each shield being independently displaceable against the spring to a retracted position wherein the piercing tip of the trocar obturator is exposed.

21 Claims, 3 Drawing Sheets

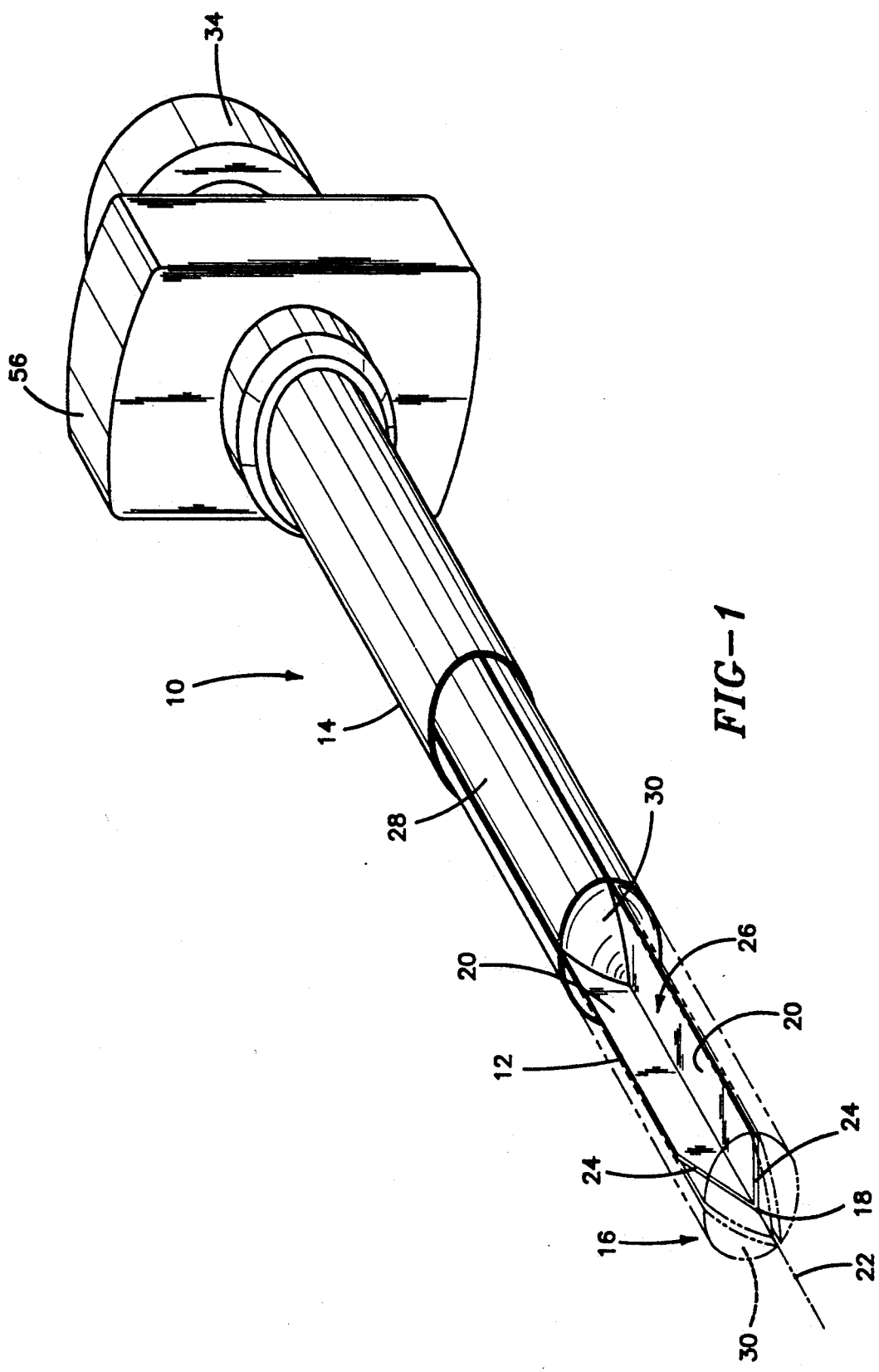

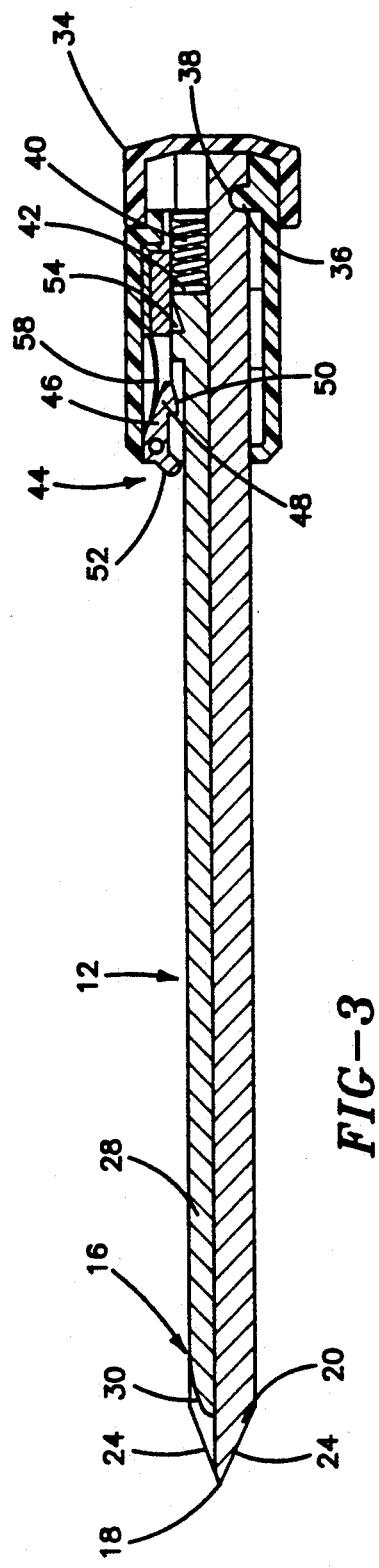
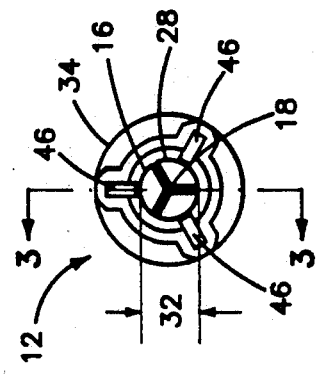
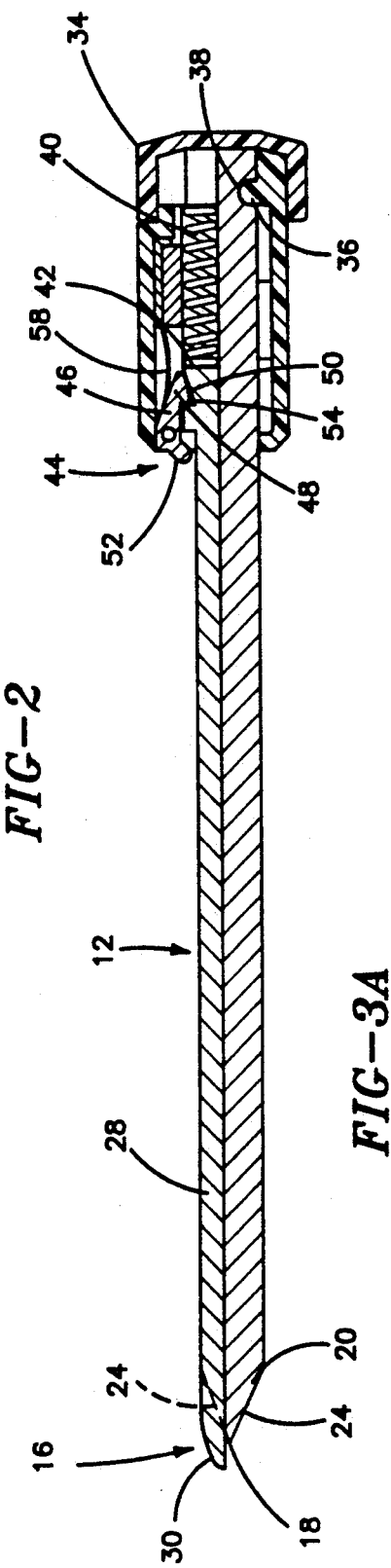

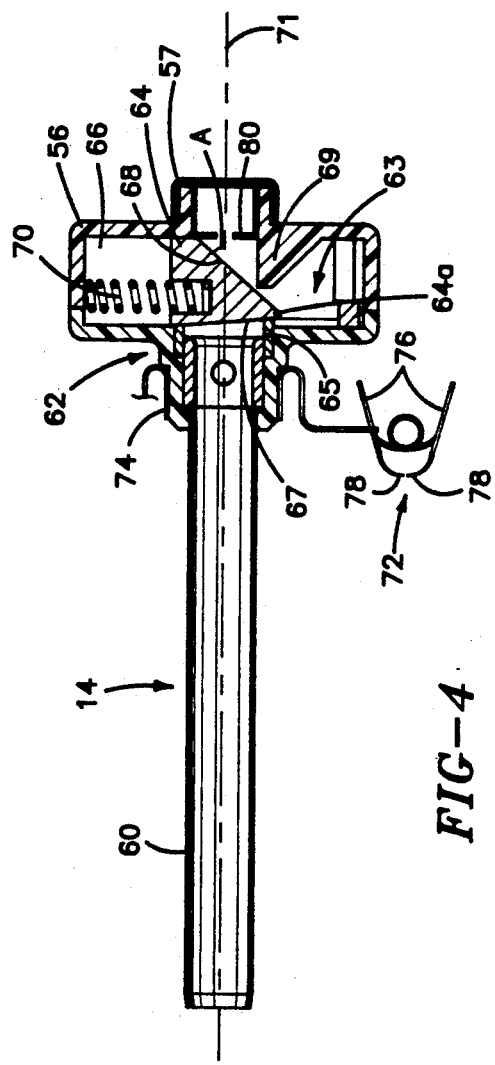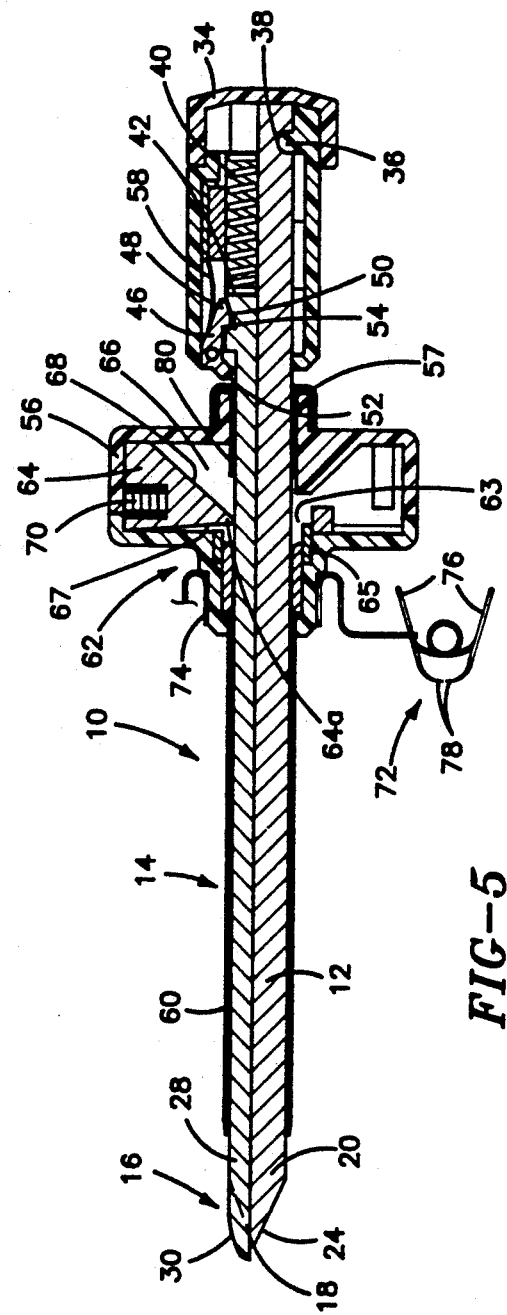

TROCAR ASSEMBLY WITH INDEPENDENTLY ACTING SHIELD MEANS

BACKGROUND OF THE INVENTION

1. Field of the Invention

The invention relates to the field of surgical instruments and, more particularly, to a trocar assembly for piercing a wall of a body cavity.

2. Description of the Related Art

A trocar is a sharp pointed instrument used in surgical procedures where it is necessary to puncture the wall of a body cavity. Such a procedure is often performed in order to drain fluids from the body cavity using a cannula inserted in the opening. Trocars are also useful in performing endoscopic procedures. In such a procedure, a preliminary puncture is generally made with a cannula so that the body cavity can be inflated with a gas in order to lift the wall of the body cavity away from other organs which may lie beneath the wall. A standard trocar, disposed in a trocar tube, is then inserted into the body cavity through the first puncture. The trocar is then removed leaving the trocar tube in place and endoscopic instruments can then be inserted through the trocar tube.

Standard trocars are generally metal rods having a sharpened point, frequently of surgical steel. A commonly encountered problem associated with the use of trocar is that a significant risk exists that the trocar will pierce the wall of the body cavity and injure internal organs lying thereunder. Numerous disclosures have been made wherein this problem is addressed by disposing a spring biased shield over the trocar. The shield is pressed back or retracted when the instrument is pressed against a wall of a body cavity, thus exposing the piercing tip of the trocar. When the trocar has completely penetrated the wall, the shield is pushed forward to an extended position to shield the piercing tip of the trocar. Examples of patents dealing with this type of structure include U.S. Pat. No. 4,654,030 to Moll et al, U.S. Pat. No. 4,601,710 to Moll, and U.S. Pat. No. 4,535,773 to Yoon.

According to the prior art, the shield is a concentric sleeve which is disposed over the trocar and thus has a larger diameter than the trocar. Further, the trocar and shield are disposed for use in a trocar tube of still larger diameter. Thus, the piercing tip of the trocar is of the smallest diameter of all instruments which are to enter the cavity through the wall where it is pierced. In operation, such devices result in a stretching and tearing of the wound in order to accommodate the larger diameter of the shield and the further larger diameter of the trocar tube.

Further, the piercing tip cannot be shielded until the entire shield has entered the wound. Thus, such devices still allow a significant risk of injury to organs and other tissue lying beneath the wall to be pierced.

It is thus the principal object of the present invention to provide a trocar assembly having a shield which can be disposed for use with a minimum amount of stretching, and no tearing, of the wound made by the trocar.

It is a further object of the present invention to provide a trocar assembly having a shield which can more reliably and readily deploy to shield the piercing point of the trocar.

Other objects and advantages of the invention will become readily apparent to one skilled in the art upon a consideration of the following disclosure.

SUMMARY OF THE INVENTION

The foregoing objects and advantages are readily attained by the trocar assembly of the present invention.

According to the invention, the assembly includes a trocar obturator having an outer diameter, a piercing tip and at least one, preferably a plurality of longitudinal cutouts; and means for shielding said piercing tip, mounted in said longitudinal cutouts so as to be movable between an extended position and a retracted position, said shield means being adapted to fit inside said longitudinal cutouts so as to shield said piercing tip when said shield means is in said extended position without exceeding said outer diameter of said trocar obturator.

According to a preferred embodiment of the invention, said shield means comprises a plurality of independently acting shield means mounted in said plurality of longitudinal cutouts, and said trocar assembly further comprises means for independently biasing each of said plurality of shield means toward said extended position wherein said piercing tip of said trocar obturator is shielded, each of said plurality of shield means being independently displaceable against said biasing means to said retracted position wherein said piercing tip of said trocar obturator is exposed. Said plurality of independently acting shield means may preferably be like in number to said plurality of longitudinal cutouts, each shield means being mounted in a respective longitudinal cutout.

According to a still further preferred embodiment of the invention, the assembly includes means for independently locking each of said plurality of shield means in said extended position, said locking means being disposed in said housing.

Means for clipping the trocar tube in place to the body may preferably also be included according to the present invention.

BRIEF DESCRIPTION OF THE DRAWINGS

A detailed description of the invention follows, with reference to the accompanying drawings, in which:

FIG. 1 is a perspective view of a trocar assembly, according to the invention;

FIG. 2 is an end view of a trocar obturator, according to the invention;

FIG. 3 is a sectional view, taken along the lines 3—3 of FIG. 2, of the trocar obturator according to the invention, with shield means in a retracted position;

FIG. 3A is a sectional view of the assembly of FIG. 3 with shield means in a locked extended position;

FIG. 4 is a side view of a preferred embodiment of a trocar tube with clipping means and valve assembly in closed position, in section, according to the invention; and FIG. 5 is a side view, in section, of the trocar tube of FIG. 4 with the trocar obturator of FIG. 3 disposed therein for use.

DESCRIPTION OF THE PREFERRED EMBODIMENTS

The invention pertains to a surgical instrument, namely a trocar assembly, for piercing the wall of a body cavity for various surgical procedures such as endoscopy and drawing off of fluids.

A trocar is an elongated rod or peg with a sharpened point. With reference to FIG. 1, a trocar assembly according to the invention is referred to generally by the reference numeral 10. The trocar assembly 10 comprises a trocar obturator 12, a trocar tube 14, and shield means 16, said shield means being slidably disposed relative to trocar obturator 12 between an extended position, shown in FIG. 1 in phantom lines, and a retracted position as shown in FIG. 1 in full lines.

Trocar obturator 12 preferably comprises a generally elongated member having a sharpened point or piercing tip 18. According to the invention, trocar obturator 12 preferably comprises a plurality of blades 20 which are joined at a central axis 22 of trocar obturator 12. Each blade 20 has a sharpened angle surface 24. Angle surfaces 24 of blades 20, in conjunction, form piercing tip 18. At least one longitudinal cutout, preferably a plurality of longitudinal cutouts 26, are formed between each pair of blades 20.

Shield means 16 preferably comprises a plurality of rods 28, preferably equal in number to the number of longitudinal cutouts 26 located in trocar obturator 12. For example, as shown in the drawing, three rods 28 may be disposed in three longitudinal cutouts 26. Rods 28 are blunted or rounded at an end 30 corresponding to piercing tip 18 of trocar obturator 12. In the extended position, shield means 16 extend beyond tip 18 of trocar obturator ;2 so as to protect and shield piercing tip 18 while the trocar assembly 10 is stored or handled. As more thoroughly described below, shield means 16 also serves to shield piercing tip 18 after trocar obturator 12 has pierced a wall (not shown) of a body cavity.

FIG. 2 shows a front view of trocar obturator 12, according to the invention. Blades 20 of trocar obturator 12 define a diameter 32. Rods 28 of shield means 16 are mounted in longitudinal cutouts 26 and shaped, preferably as sections of a cylinder having a diameter no greater than the diameter defined by blades 20 of trocar obturator 12, so as to present a generally round profile which does not exceed diameter 32 of trocar obturator 12. In this fashion, and advantageously, shield means 16 can deploy to shield piercing tip 18 during use of the instrument, without enlarging the wound formed by trocar obturator 12. This is due to the disposition within cutouts 26 (as clearly shown in FIG. 1) of shield means 16 which, according to the invention, presents a shield means having a diameter which is substantially the same as that defined by blades 20 of trocar obturator 12.

It should be noted that while a generally round profile of trocar obturator 12 and shield means 16 is preferred, the profile may of course differ as dictated by the shape of the instrument to be used. Thus, the profile could, for example, be elliptical, obround, or oblong round flatted round or the like.

FIGS. 3, 3A show a sectional view of a trocar obturator 12 according to the invention, taken along lines 3—3 of FIG. 2. FIG. 3 illustrates a retracted position of rods 28 of shield means 16. FIG. 3A illustrates a locked extended position of rods 28 of shield means 16. As shown, trocar obturator 12 is preferably fixedly and non-rotatably mounted in a trocar housing 34. This mounting may preferably be accomplished by assembling trocar housing 34 around trocar obturator 12. Post 36 at housing 34 may preferably be arranged in registry with notch 38 of trocar obturator 12 so as to provide desired non-rotatable mounting and retention. Rods 28 are slidably disposed in longitudinal cutouts 26 (see FIG. 1) between trocar obturator 12 and trocar housing 34. Biasing means 40, for example, a spring or the like, are disposed in trocar housing 34 so as to press against rearward ends 42 of rods 28, thereby biasing rods 28 into the locked and extended or shielding position of FIG. 3A. Each rod 28 is preferably independently biased by biasing means 40, as for example by using a separate biasing means for each rod 28. In this manner, piercing tip 18 is shielded as soon as any one rod 28 is free to extend. Shield means made of a single integral shield member cannot deploy to shield piercing tip 18 until the entire shield member is free to enter the wound. Thus, the shield means of the present invention allows a more rapid and reliable shielding of piercing tip 18, and a concomitant reduction in risk of injury to organs lying beneath the pierced Wall of the body cavity.

Ends 30 of rods 28 are blunted and, according to the invention, are preferably rounded or sloped as shown in the drawing so as to facilitate entry of rods 28 into the wound formed by trocar obturator 12. In this manner, each rod is free to extend into the wound and shield piercing tip 18 with a minimum amount of resistance from the wound.

Trocar housing 34 also preferably contains locking means 44 for releasably locking shield means 16 in the extended position. In the locked extended position, shield means 16 is locked in place and cannot be retracted until locking means 44 is released. Locking means 44 preferably comprise one or more latch mechanisms, or levers 46, pivotably disposed within trocar housing 34. Each lever 46 has a rearwardly disposed first end 48 having a projection 50, and a forwardly disposed second end 52 protruding from trocar housing 34. Projection 50 is disposed in alignment with a notch 54 formed in rod 28, so that projection 50 enters notch 54 when rod 28 is biased to the extended position as shown in FIG. 3A. Second end 52 of lever 46 allows rod 28 to be released from a locked extended position, by pivoting lever 46 to withdraw projection 50 from notch 54 to enable rearward displacement of rod 28 as will be discussed below. Pivoting of lever 46 may be accomplished, for example, by direct manipulation of lever 46, or by contact of lever 46, preferably with tube housing cap 57 of tube housing 56 (as shown in FIG. 5), when trocar obturator 12 is moved into trocar tube 14. According to a preferred embodiment of the invention, lever 46 may be biased into locking engagement with notch 54 by biasing means such as leaf spring 58 or the like. Preferably, a separate locking means 44 (lever 46) could be provided for each rod 28 independently, as shown for example in FIG. 2. For simplicity, only a single locking means 44 is shown in the cross sections of FIGS. 3, 3A. Trocar housing 34 and lever 46 also serve to define the limits of longitudinal displacement (extension and retraction) for rods 28.

FIG. 4 shows a preferred embodiment of a trocar tube 14, according to the invention. Trocar tube 14 is a generally elongated round tube 60 mounted in a tube housing 56. Trocar tube 14 is sized so as to slidably receive trocar obturator 12, as described below with reference to FIG. 5. As with trocar obturator 12 and shield means 16, trocar tube 14 is preferably round in shape, but may of course be of any different shape convenient to accommodate instruments of different shape. Trocar tube 14 preferably has a valve means 62 mounted in tube housing 56. Valve means 62 preferably comprises a piston 64, preferably rectangular or square in shape, mounted in a cylinder 66 in tube housing 56.

Piston 64 preferably has a wedge shaped opening 63 through which instruments such as trocar obturator 12 pass when valve means 62 is in the open position. Piston 64 of valve means 62 serves to seal trocar tube 14 when trocar tube 14 is inserted into a body cavity and trocar obturator 12 is removed therefrom. Piston 64 also preferably has an angular face 68 disposed at the wedge shaped opening 63 thereof, and facing an opening of the tube housing 56 through which trocar obturator 12 is to be inserted. Angular face 68 of piston 64 serves to slide piston 64 out of the way, into cylinder 66, when a tool or trocar obturator 12 is inserted into tube housing 56 of trocar tube 14. Angular face 68 may preferably have an angle A, relative to a longitudinal axis 71 of trocar tube 14, of about 45 degrees. Biasing means 70, such as a spring or the like, are preferably disposed in cylinder 66 to bias piston 64 toward a closed position. Cylinder 66 is preferably rectangular or square in shape so as to accommodate piston 64.

A sealing collar 65 is preferably disposed in tube housing 56. Further, piston 64 preferably has a slightly tapered or angled side 67 facing toward trocar tube 14 and sealing collar 65. Angled side 67 preferably tapers away from sealing collar 65 at end 64a of piston 64. Sealing collar 65 interacts with angled side 67 of piston 64 so as to provide an effective seal of trocar tube 14 when no instrument is inserted into trocar tube 14, and piston 64 is closed. Sealing collar 65 may also be extended toward angled side 67 at a portion corresponding to end 64a of piston 64. In this manner, when piston 64 is in the closed position, sealing collar 65 sealingly engages angled side 67, and when piston 64 is opened, sealing collar 65 readily disengages from side 67 to minimize resistance to sliding of piston 64.

Guide means 69 are also preferably arranged in tube housing 56. Guide means 69 serve to guide an instrument, such as trocar obturator 12, into trocar tube 14 and prevent misalignment which may be caused by deflection of the instrument due to contact with angular face 68 of piston 64 when the instrument is inserted into trocar tube 14. Guide means 69 may also suitably be positioned in tube housing 56 so as to serve as a stop for piston 64 when piston 64 is moved into the closed position of FIG. 4.

According to a preferred embodiment of the invention, clipping means 72 may be disposed on trocar tube 14 in order to secure trocar tube 14 in place in a body cavity against pressure exerted thereon. Clipping means 72 may preferably comprise a flexible boot 74 removably and/or slidably disposed over tube housing 56 and tube 60 and having a plurality of clips 76 mounted thereon. Each clip 76 preferably comprises a spring formed wire with needle tips 78. After trocar tube 14 is in place, it may be secured by pinching clip 76 to open needle tips 78, which are disposed onto the skin of a patient being treated, or onto a holding means, and released. Needle tips 78 will hold trocar tube 14 in place and can be released by pinching clip 76 to withdraw needle tips 78 and release the clip. Boot 74 is slidably disposed on tube 60 so that inadvertent removal of trocar tube 14 without releasing needle tips 78 will not result in a tearing of the skin of the patient. Rather, boot 74 will slide down along tube housing 56 and tube 60 and can subsequently be removed.

According to the invention, sealing means such as membrane 80 may be disposed in tube housing 56. Membrane 80 may be disposed in tube housing 56 in any convenient manner and may, for example, be held by tube housing cap 57 as shown. Trocar obturator 12 or other instruments to be used may have a smaller diameter than the inside diameter of trocar tube 14. Membrane 80 serves to provide a seal between tube housing 56 and such other instruments, which may be inserted through tube housing 56 of trocar tube 14.

FIG. 5 is a sectional view showing trocar obturator 12 disposed for use inside trocar tube 14. This drawing illustrates the operation of piston 64. When an instrument such as trocar obturator 12 is inserted into trocar tube 14, piston 64 displaces within tube housing 56 as shown, thus allowing trocar obturator 12 to pass through tube housing 56 and into trocar tube 14. Piston 64 is displaced into tube housing 56 by contact between angular face 68 and shield means 16 or trocar obturator 12. FIG. 5 also illustrates one configuration of lever 46 wherein contact between tube housing 56 and second end 52 of lever 46 causes locking means 44 to release shield means 16 from a locked extended position.

It should be noted that trocar housing 34 and tube housing 56 could be of any desired shape other than that shown as an example in the drawings. By way of further example, these housings could be shaped to more conveniently and comfortably fit the hand.

With general reference to FIGS. 1-5, the trocar assembly according to the invention operates as follows.

Prior to use, trocar obturator 12 is disposed in trocar tube 14. Shield means 16 are locked into an extended position by locking means 44, thus shielding piercing tip 18 for storage and handling prior to use.

When the trocar assembly is to be used, shield means 16 can be unlocked by manipulating lever or levers 46, for example through contact with tube housing cap 57. When trocar obturator 12 is pressed all the way into trocar tube 14, second end 52 of lever 46 contacts housing cap 57 and is pressed, pivoting lever 46 in a counter-clockwise direction, as viewed in the drawing, thereby removing projection 50 from notch 54, and releasing shield means 16 from the locked extended position.

Trocar obturator 12 is positioned in a desired location of a patient to be treated, against a wall of a body cavity to be pierced. Pressure exerted on trocar housing 34 of trocar obturator 12 will push shield means 16 against the skin of the patient. This pushing will cause the unlocked shield means to retract, or displace rearwardly in longitudinal cutouts 26, exposing piercing tip 18. Piercing tip 18 pierces the skin of the patient and the wall of the body cavity. Rods 28 are independently biased forward, toward a shielding position, by biasing means 40. As piercing tip 18 penetrates into the body cavity, one or more rods 28 will slide forward into the extended position, thereby shielding internal organs and other tissues from inadvertent damage from piercing tip 18. Because rods 28 are biased independently, shielding takes place as soon as any one rod 28 is free to enter the body cavity. Thus, shielding takes place more quickly and reliably than is possible with prior art devices having concentric shields.

Also, because shield means 16 has a diameter of the same size as trocar obturator 12, and subsequently, the same size as the opening formed in the wall of the body cavity, no stretching or tearing takes place upon the extension of the shield means 16, and only a minimum amount of stretching occurs upon insertion of trocar tube 14.

Trocar tube 14 can be held in place by clipping means 72. Clips 76 are opened and disposed either on a holding means or the skin of the patient, where they serve to hold trocar tube 14 firmly but tractably in place.

Trocar obturator 12 can now be removed from trocar tube 14 to allow the intended surgical procedure to be performed. When trocar obturator is removed, piston 64 closes valve means 62, thus sealing off trocar tube 14 by means of sealing collar 65. When another instrument is to be inserted, such as an endoscopic tool (not shown), the tip of the tool contacts angular face 68 of piston 64 and displaces piston 6 into tube housing 56 in a similar fashion to that shown in FIG. 5. The valve can also be manually opened by an outside lever (not shown).

Trocar tube 14 can be removed, when desired, by pinching clips 76 to release clipping means 72 from the patient. If clipping means 72 is not released prior to removal of trocar tube 14, boot 74 slides down tube housing 56 and tube 60 of trocar tube 14 from where it can be removed later, thus avoiding injury to the patient.

Thus disclosed is a trocar assembly which provides for use with less stretching and no tearing of the wall of the body cavity, and which provides a more rapid and reliable deployment of the shield over the piercing tip of the trocar obturator, thus providing safer surgical procedures.

This invention may be embodied in other forms or carried out in other ways without departing from the spirit or essential characteristics thereof. The presently described embodiments are therefore to be considered as in all respects illustrative and not restrictive, the scope of the invention being indicated by the appended claims, and all changes which come within the meaning and range of equivalency are intended to be embraced therein.

What is claimed is:

1. A trocar assembly, comprising:
    a trocar obturator having an outer diameter, a plurality of blades joined together and forming a piercing tip, and a plurality of longitudinal cutouts formed between said plurality of blades;
    a plurality of independently acting shield means for shielding said piercing tip, mounted in said plurality of longitudinal cutouts so as to be movable between an extended position wherein said piercing tip is shielded, and a retracted position wherein said piercing tip is exposed, said plurality of shield means having a diameter substantially the same as said outer diameter of said trocar obturator; and
    means for independently biasing each of said plurality of shield means toward said extended position.

2. A trocar assembly according to claim 1, wherein each of said plurality of shield means is independently displaceable against said biasing means to said retracted position.

3. A trocar assembly according to claim 2, wherein said plurality of shield means are like in number to said plurality of longitudinal cutouts.

4. A trocar assembly according to claim 1, wherein said plurality of shield means comprises a plurality of elongate rods each having a blunt end at an end corresponding to said piercing tip of said trocar obturator.

5. A trocar assembly according to claim 4, wherein each of said plurality of elongate rods is shaped as a section of a cylinder having a diameter no greater than said outer diameter of said trocar obturator.

6. A trocar assembly according to claim 5, wherein each said blunt end of said plurality of rods is sloped whereby entry of each of said plurality of rods into a wound formed by said trocar obturator is facilitated.

7. A trocar obturator having an outer diameter, a plurality of blades joined together and forming a piercing tip, and a plurality of longitudinal cutouts formed between said plurality of blades;
    a plurality of independently acting shield means for shielding said piercing tip, mounted in said plurality of longitudinal cutouts so as to be movable between an extended position wherein said piercing tip is shielded, and a retracted position wherein said piercing tip is exposed, said plurality of shield means having a diameter substantially the same as said outer diameter of said trocar obturator; and
    means for independently locking each of said plurality of shield means in said extended position.

8. A trocar assembly according to claim 7, further comprising a housing, said trocar obturator being mounted in said housing, said plurality of shield means being slidably disposed between said trocar obturator and said housing.

9. A trocar assembly according to claim 8, wherein said locking means is disposed in said housing.

10. A trocar assembly according to claim 9, wherein said locking means comprises a plurality of latch means for independently and releasably locking each of said shield means in said extended position to shield said piercing tip.

11. A trocar assembly according to claim 10, wherein each of said plurality of latch means comprises a lever, pivotally mounted in said housing and having a first end having a projection in registry with a notch in a respective shield means when said respective shield means is in said extended position, and said lever having a second end protruding from said housing whereby said lever can be pivoted so as to release said shield means for displacement to said retracted position.

12. A trocar assembly, comprising:
    a trocar obturator having a piercing tip and a plurality of longitudinal cutouts;
    a trocar tube in which said trocar obturator is housed;
    a plurality of means for shielding said piercing tip mounted in said longitudinal cutouts so as to be movable between an extended position and a retracted position; and
    means for independently biasing each of said plurality of shield means toward said extended position wherein said piercing tip of said trocar obturator is shielded, each of said plurality of shield means being independently displaceable against said biasing means to said retracted position wherein said piercing tip of said trocar obturator is exposed.

13. A trocar assembly according to claim 12, further comprising:
    a tube housing in which said trocar tube is mounted; and
    valve means slidably disposed in said tube housing between a closed position wherein said trocar tube is sealed and an open position wherein said trocar obturator is inserted through said tube housing and said trocar tube.

14. A trocar assembly according to claim 13, wherein said valve means comprises a piston mounted for displacement in said tube housing.

15. A trocar assembly according to claim 14, further comprising means for biasing said piston toward a closed position, and wherein said piston has an angular face on a side facing an opening of said tube housing so that, when said trocar obturator is inserted into said tube housing, and contacts said angular face, said piston is displaced toward an open position.

16. A trocar assembly according to claim 15, wherein said angular face forms an angle with a longitudinal axis of said trocar tube, said angle being approximately 45 degrees.

17. A trocar assembly according to claim 16, further comprising a sealing collar disposed in said tube housing and interacting with said piston to provide a seal when said piston is in said closed position.

18. A trocar assembly according to claim 17, wherein said piston has an angled side facing said sealing collar and tapering away from said sealing collar whereby, when said piston is in said closed position, said sealing collar sealingly engages said angled side, and when said piston is opened, said sealing collar disengages from said angled side.

19. A trocar assembly according to claim 18, further comprising guide means, disposed within said tube housing, said guide means serving to guide said trocar obturator into said trocar tube so as to prevent misalignment of said trocar obturator due to contact with said angular face of said piston.

20. A trocar assembly according to claim 12, further comprising means for clipping said trocar tube in place in a wall of a body cavity when said trocar assembly is in use, said clipping means comprising a boot, removably disposed on said trocar tube and having a plurality of clips for releasable attachment to a wall of a body cavity.

21. A trocar assembly, comprising:
a trocar obturator having an outer diameter, a piercing tip and at least one longitudinal cutout;
a trocar tube in which said trocar obturator is housed;
means for shielding said piercing tip, mounted in said at least one longitudinal cutout so as to be movable between an extended position and a retracted position, said shield means being adapted to fit inside said at least one longitudinal cutout so as to shield said piercing tip when said shield means is in said extended position without exceeding said outer diameter of said trocar obturator; and
means for clipping said trocar tube in place in a wall of a body cavity when said trocar assembly is in use, said clipping means comprising a boot, removably disposed on said trocar tube and having a plurality of clips for releasable attachment to a wall of a body cavity.

* * * * *